United States Patent
Schabbach et al.

(10) Patent No.: US 12,337,144 B2
(45) Date of Patent: Jun. 24, 2025

(54) MEDICAMENT DELIVERY DEVICE

(71) Applicant: Sanofi, Paris (FR)

(72) Inventors: Michael Schabbach, Frankfurt am Main (DE); Beate Franke, Frankfurt am Main (DE); Giuliano Pradel, Besana in Brianza (IT); Andrew Nelson, Dallas, TX (US)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 18/638,166

(22) Filed: Apr. 17, 2024

(65) Prior Publication Data

US 2024/0261507 A1  Aug. 8, 2024

Related U.S. Application Data

(63) Continuation of application No. 17/526,268, filed on Nov. 15, 2021, now Pat. No. 11,986,634, which is a (Continued)

(30) Foreign Application Priority Data

Jul. 14, 2016 (EP) ..................... 16305915

(51) Int. Cl.
*A61M 5/20* (2006.01)
*A61M 5/24* (2006.01)
*A61M 5/32* (2006.01)

(52) U.S. Cl.
CPC ............... *A61M 5/20* (2013.01); *A61M 5/24* (2013.01); *A61M 5/326* (2013.01);
(Continued)

(58) Field of Classification Search
CPC ...... A61M 5/20; A61M 5/24; A61M 5/31566; A61M 5/321; A61M 5/3234;
(Continued)

(56) References Cited

U.S. PATENT DOCUMENTS 8,292,849 B2  10/2012  Bobroff et al.
9,022,979 B2  5/2015  Woehr
(Continued)

FOREIGN PATENT DOCUMENTS

CN  1376524  10/2002
CN  103945879  7/2014
(Continued)

OTHER PUBLICATIONS

International Preliminary Report on Patentability in Application No. PCT/EP2017/067512, Jan. 15, 2019, 11 pages.
(Continued)

*Primary Examiner* — Joel M Attey
*Assistant Examiner* — Alexandra Lalonde
(74) *Attorney, Agent, or Firm* — Fish & Richardson P.C.

(57) ABSTRACT

A medicament delivery device includes a device housing for placing on skin of a patient, the device housing including a needle aperture; a needle for injecting 5 a medicament, the needle arranged to pass through the needle aperture; and sensors configured to provide a signal when the device housing is placed on the skin of the patient. The sensors are arranged around the needle aperture.

19 Claims, 5 Drawing Sheets

Related U.S. Application Data continuation of application No. 16/317,633, filed as application No. PCT/EP2017/067512 on Jul. 12, 2017, now Pat. No. 11,173,247.

(52) U.S. Cl.
CPC . *A61M 2005/206* (2013.01); *A61M 2005/208* (2013.01); *A61M 5/3243* (2013.01); *A61M 2205/13* (2013.01)

(58) Field of Classification Search
CPC .. A61M 5/3243; A61M 5/326; A61M 5/3271; A61M 5/3272; A61M 5/1428; A61M 5/3205; A61M 5/3257; A61M 5/3287; A61M 2005/2073; A61M 2005/208; A61M 2005/3236; A61M 2005/3247; A61M 2005/325; A61M 2005/3252; A61M 2005/3256; A61M 2005/3258; A61M 2005/3263; A61M 2005/3265; A61M 2005/206; A61M 2005/3254; A61M 2005/2013; A61M 2005/14252; A61M 2005/14256; A61M 2005/1426; A61M 2005/3022; A61M 2005/14264; A61M 2005/1585; A61M 2005/1586; A61M 2205/13; A61M 2205/33; A61M 2205/3306; A61M 2205/3327; A61M 2205/3331; A61M 2205/3368; A61M 2230/005; A61M 2230/50; A61M 5/3245; A61M 2210/04

See application file for complete search history.

(56) References Cited

U.S. PATENT DOCUMENTS

| | | |
|---|---|---|
| 11,173,247 B2 | 11/2021 | Schabbach et al. |
| 11,986,634 B2 | 5/2024 | Schabbach et al. |
| 2004/0199123 A1* | 10/2004 | Nielsen ............... A61M 5/14 424/449 |
| 2009/0024112 A1 | 1/2009 | Edwards et al. |
| 2013/0218129 A1 | 8/2013 | Clarke et al. |
| 2014/0142507 A1 | 5/2014 | Armes |
| 2014/0335495 A1 | 11/2014 | Baker et al. |
| 2016/0089056 A1 | 3/2016 | Limaye et al. |
| 2016/0106921 A1* | 4/2016 | Fraunhofer ....... A61M 5/14244 604/89 |
| 2016/0228644 A1* | 8/2016 | Cabiri ................ A61M 5/142 |
| 2016/0296699 A1* | 10/2016 | Cabiri .................. A61M 5/20 |
| 2017/0182242 A1* | 6/2017 | Galitz .................. A61M 5/20 |
| 2017/0232204 A1 | 8/2017 | Knapp et al. |
| 2017/0354780 A1 | 12/2017 | Park et al. |
| 2018/0318526 A1* | 11/2018 | Yang ................. A61M 5/3204 |
| 2019/0262538 A1 | 8/2019 | Schabbach et al. |
| 2022/0072230 A1 | 3/2022 | Schabbach et al. |

FOREIGN PATENT DOCUMENTS

| | | |
|---|---|---|
| CN | 104780961 | 7/2015 |
| CN | 105473173 | 4/2016 |
| EP | 3000497 | 3/2016 |
| JP | 2016-067936 | 5/2016 |
| JP | 2017-520298 | 7/2017 |
| JP | 2017-526488 | 9/2017 |
| WO | WO 2014/025796 | 2/2014 |
| WO | WO 2014/066256 | 5/2014 |
| WO | WO 2015/014363 | 2/2015 |
| WO | WO 2015/187797 | 12/2015 |
| WO | WO 2016/041876 | 3/2016 |

OTHER PUBLICATIONS

International Search Report and Written Opinion in Application No. PCT/EP2017/067512, dated Dec. 6, 2017, 15 pages.

* cited by examiner

MEDICAMENT DELIVERY DEVICE

CROSS REFERENCE TO RELATED APPLICATIONS

The present application is a continuation of U.S. patent application Ser. No. 17/526,268, filed on Nov. 15, 2021 and issued as U.S. Pat. No. 11,986,634 on May 21, 2024, which is a continuation of U.S. patent application Ser. No. 16/317,633, filed on Jan. 14, 2019 and issued as U.S. Pat. No. 11,173,247 on Nov. 16, 2021, which is the national stage entry of International Patent Application No. PCT/EP2017/067512, filed on Jul. 12, 2017, and claims priority to Application No. EP 16305915.7, filed on Jul. 14, 2016, the disclosures of which are incorporated herein by reference.

TECHNICAL FIELD

The present disclosure relates to a device for delivery of medicament to a patient.

BACKGROUND

A variety of diseases exist that require regular treatment by injection of a medicament and such injections can be performed by using injection devices. Injection or infusion pumps of the type known as patch pumps for delivering injections of medicament are known in the art. Another type of injection pump that is gaining traction is the bolus injector device. Some bolus injector devices are intended to be used with relatively large volumes of medicament, typically at least 1 ml and may be a few ml. Injection of such large volumes of medicament can take some minutes or even hours. Such high capacity bolus injector devices can be called large volume devices (LVDs). Generally such devices are operated by the patients themselves, although they may also be operated by medical personnel.

To use a patch pump or bolus injector device, such as an LVD, it is first supported on a suitable injection site on a patient's skin. Once installed, injection is initiated by the patient or another person (user). Typically, the initiation is effected by the user operating an electrical switch, which causes a controller to operate the device. Operation includes firstly injecting a needle into the user and then causing the injection of medicament into the user's tissue. Biological medicaments are being increasingly developed which comprise higher viscosity injectable liquids and which are to be administered in larger volumes than long-known liquid medicaments. LVDs for administering such biological medicaments may comprise a pre-filled disposable drug delivery device or, alternatively, a disposable drug delivery device into which a patient or medical personnel must insert a drug cartridge prior to use.

SUMMARY

According to an aspect a medicament delivery device is provided including a device housing for placing on the skin of a patient, the housing including a needle aperture; a needle for injecting a medicament, the needle arranged to pass through the needle aperture; and a plurality of sensors configured to provide a signal when the housing is placed on the skin of the patient, wherein the sensors are arranged around the needle aperture.

The device may include an output transducer. The plurality of sensors may provide the signal using the output transducer.

The device may include an injection mechanism for delivering the medicament through the needle. The injection mechanism may be activated conditional on the signal provided by the plurality of sensors.

The device may include a retractable needle shield which is disposed around the needle aperture. The needle shield may be retracted within the housing in a first position, and extend to surround the needle in a second position.

The plurality of sensors may be disposed on the needle shield

The needle shield may be configured to move to the second position conditional on the signal provided by the plurality of sensors.

The device may include a needle insertion mechanism, wherein the needle is disposed within the housing in an initial position, and the needle insertion mechanism is configured to move the needle through the aperture to extend from the device housing in an engaged position.

A portion of the needle may be configured to engage with the sensors in the engaged position, and the sensors may be further configured to provide a signal when the needle is in the engaged position.

The device may include a medicament reservoir and a medicament which is retained in the medicament reservoir.

According to a further aspect a method of delivering a medicament is provided, including placing a medicament delivery device on the skin of a patient; sensing, using a plurality of sensors, when a housing of the device is placed on the skin of the patient, wherein the sensors are arranged around a needle aperture of the device; and providing a signal when the housing is placed on the skin.

The method may include activating an injection mechanism for delivering the medicament through a needle, conditional on the provided signal.

The method may include extending a retractable needle shield which is disposed around the needle aperture, from a first position wherein the needle shield is retracted within the housing, to a second position wherein the needle shield surrounds the needle, conditional on the provided signal.

The method may include moving the needle through the needle aperture, from a first position wherein the needle is disposed within the housing, to an engaged position wherein the needle extends from the device housing.

The method may include sensing, using the plurality of sensors, when the needle is in the engaged position; and providing a signal when the needle is in the engaged position.

These and other aspects will be apparent from and elucidated with reference to the embodiments described hereinafter.

BRIEF DESCRIPTION OF THE DRAWINGS

Exemplary embodiments are described with reference to the accompanying drawings, in which.

DETAILED DESCRIPTION

Figure 1:
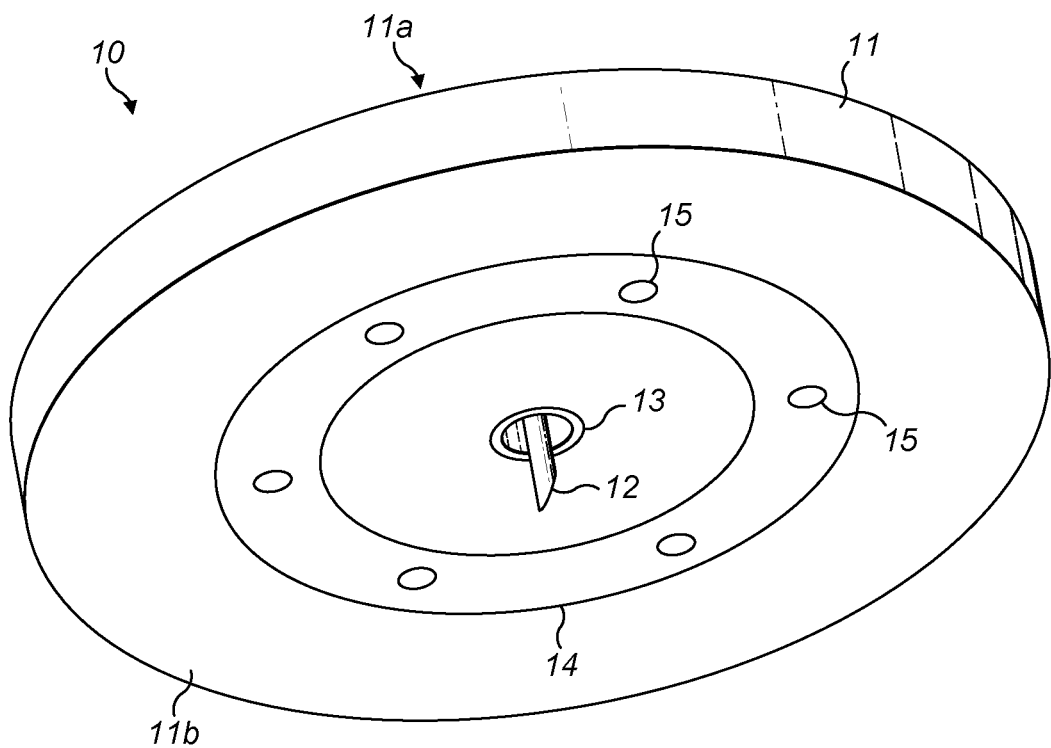
FIG. 1 is an isometric view of a medicament delivery device according to a first embodiment.

A medicament delivery device, as described herein, may be configured to inject a medicament into a patient. For example, delivery could be sub-cutaneous, intra-muscular, or intravenous. Such a device could be operated by a patient or by a care-giver, such as a nurse or physician. The device can include a cartridge-based system that requires piercing a sealed ampule before use. The device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g. about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The medicament delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of a device may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a trigger against their body in order to cause injection of a medicament.

Other devices may require a multi-step activation of an automated function. For example, a user may be required to depress a button and deploy a needle in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some medicament delivery devices can also include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

With respect to FIG. 1, a medicament delivery device 10 is provided, which in the exemplary embodiment comprise a bolus injector device (hereafter simply referred to as "device 10"), according to a first embodiment which comprises a housing 11 containing a medicament delivery mechanism (not shown). The device 10 can include an LVD. The medicament delivery device is only shown schematically and a number of the functional components are omitted for the sake of clarity and brevity, but the medicament delivery mechanism includes a needle 12 for injection of the liquid medicament into a patient's body. The liquid medicament may be provided in a reservoir (not shown) within the housing 11, or may be provided externally of the device 10.

Although not shown in the figures, a medicament delivery mechanism of a device may include one or more of the following components. A controller configured to control operation of the device 10. A needle insertion mechanism to insert the needle 12 into a patient from a retracted position into an engaged position. A needle driver to drive the needle insertion mechanism, for example an electric motor or a spring mechanism. An energy source to power the needle driver. A medicament reservoir containing a supply of medicament to be administered to a patient. The medicament reservoir may for example, include a cartridge or a vial formed of glass. A plunger may be provided within the cartridge and plunger driver mechanically coupled to the plunger. The plunger driver may be controllable to move the plunger along the medicament cartridge. The force provided by the plunger causes medicament to be expelled through a medicament delivery aperture in the medicament cartridge and along a medicament delivery tube to the needle 12 to be expelled through the bore of the needle 12. An electrical power source in the form of a battery to power to the controller. The battery may also provide electrical power the plunger driver, if this is an electrically driven device. The battery may also constitute the energy source for the needle driver.

The device 10 generally comprises a housing upper side 11a and a lower side 11b, and in use, the lower side 11b of the housing 11 is intended to be a contact surface that is placed against a patient's skin during a medicament administration process. The contact surface or lower side 11b of the housing 11 includes an aperture 13 through which the needle 12 can project in use. The needle 12 of the medicament delivery device 10 is moveable between a retracted position and an engaged position. In the retracted position the needle 12 is disposed within the housing 11 of the device 10, and in the engaged position, the needle 12 projects from the lower side 11b of the housing 11 through the aperture 13 so as to pierce and inject a patient's skin when the device 10 is attached to a patient.

The device 10 comprises a sensor array 14. The sensor array 14 is disposed on the lower side 11b of the housing 11. The sensor array 14 is arranged around the aperture 13. The sensor array 14 is configured to detect when the device 10 is attached to a patient. The sensor array 14 is configured to provide a signal when the device 10 is attached to a patient. The sensor array 14 can be used to ensure that the device 10 is correctly attached to the patient before the needle 12 is moved to the engaged position.

The device 10 may comprise a user interface (not shown), including an audio output transducer and/or an visual output transducer. For example, the device 10 may include one or more of a speaker, a light or a display. The sensor array 14 may provide the signal to a patient via the user interface. The signal may be provided to a controller, which is configured to operate the user interface in response to the signal. The device 10 may indicate to a patient through an audio or visual output that the device 10 is correctly attached and ready for the medicament administration process.

Alternatively, the sensor array 14 may be configured to provide the signal to the needle insertion mechanism. The needle insertion mechanism may be configured to move the needle to the engaged position conditional on the signal provided by the sensor array 14. For example, the needle insertion mechanism may be restricted from activating to inject the needle if the signal is not provided by the sensor array 14. The patient may activate the needle insertion mechanism only when the device 10 is correctly attached. Alternatively, the needle insertion mechanism may be configured to activate automatically on receiving the signal provided by the sensor array 14.

The device 10 can prevent the injection of a patient's skin when the device 10 is incorrectly attached to the patient. For example, the device 10 can prevent the needle 12 from being injected at an incorrect angle, which can cause discomfort. In particular, where the needle 12 is arranged to extend at an angle from the housing 11. an incorrect angle of injection may be painful to a patient. The sensor array 14 can ensure that the device 10 is correctly attached to a patient before the needle 12 is injected.

The sensor array 14 comprises a plurality of sensors 15. The individual sensors 15 are spaced apart around the aperture 13. The plurality of sensors 15 can determine an inclination of the device 10 relative to the skin of a patient if one or more of the sensors 15 do not detect the skin.

The sensor array 14 comprises six sensors 15. The sensors 15 are distributed evenly around the aperture 13. The sensors 15 form a hexagon arrangement with the aperture 13 at the centre.

The plurality of sensors 15 are configured to detect contact with the skin of the patient. Alternatively, the sensors 15 may be configured to detect proximity with the skin of the patient. The sensors 15 may be, for example, capacitive sensors, optical sensors, thermal sensors or pressure sensors. A combination of sensor types may be utilized to improve accuracy.

Figure 2A:
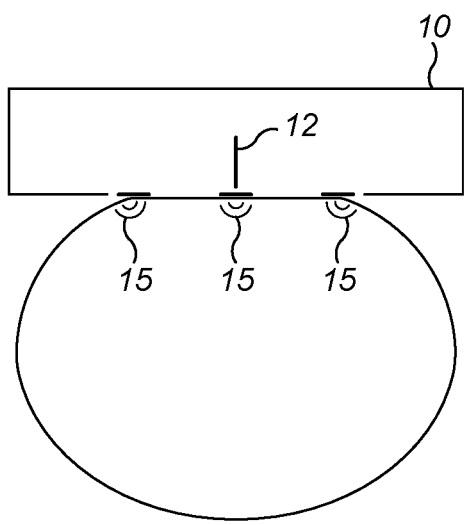
FIG. 2a is a schematic cross-section view of the FIG. 1 device in position on a patient.

FIG. 2A shows the device 10 in position with respect to a patient. The device 10 is shown in an exemplary position on an arm or leg of a patient. The device 10 is shown in a correct position, with the lower side 11b flat against the skin across the extent of the sensor array 14. Each of the sensors 15 shown is in contact with the skin. The needle 12 is perpendicular to the skin. The needle 12 is shown in the retracted position.

Figure 2B:
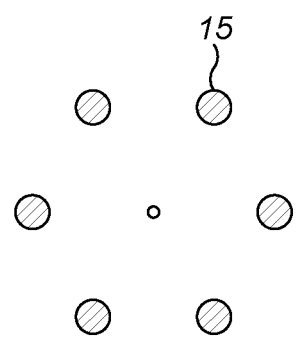
FIG. 2b is a schematic representation of an output of the FIG. 1 device.

FIG. 2B shows a representation of the output provided by the sensor array 14. The figure shows the state of the six sensors 15 surrounding the aperture 13. Each of the six sensors 15 is activated. Each of the sensors 15 is in contact with the skin when the device 10 is placed with the lower side 11b flat against the skin of a patient. When the lower side 11b is flat then the needle 12 is perpendicular to the skin. The sensor array 14 can provide a signal which indicates that the device 10 is correctly attached to the skin of a patient.

When the sensor array 14 provides a signal indicating that the device 10 is correctly attached, the needle insertion mechanism can be activated to move the needle 12 into the engaged position without causing discomfort.

Figure 3A:
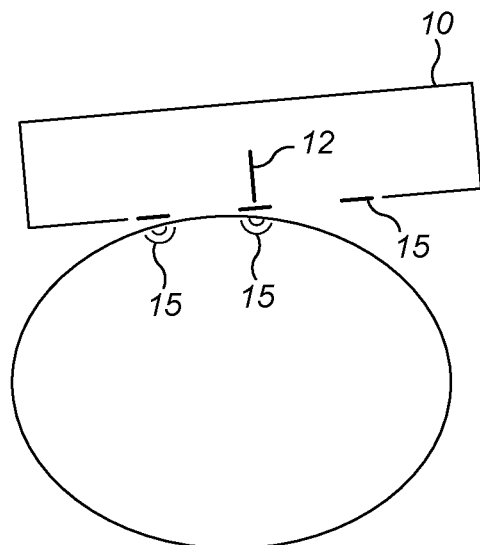
FIG. 3a is a schematic cross-section view of the FIG. 1 device in position on a patient.

FIG. 3A shows the device 10 in an incorrect position on an arm or leg of a patient. The lower side 11b of the housing 11 is not flat against the skin. The needle 12 is not perpendicular to the skin. At least one of the sensors 15 is not in contact with the skin.

Figure 3B:
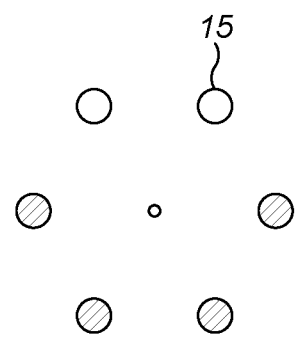
FIG. 3b is a schematic representation of an output of the FIG. 1 device.

As shown in FIG. 3B, two of the six sensors 15 are not activated. The active sensors 15 are in contact with the skin but the inactive sensors 15 are not in contact with the skin. A portion of the sensor array 14 is not activated when the device 10 is not placed with the lower side 11b flat against the skin of the patient. The needle 12 is not perpendicular to the skin and may cause discomfort if injected in the incorrect position.

The sensor array 14 does not provide a signal which indicates that the device 10 is correctly attached to the skin of a patient. The needle insertion mechanism may be prevented from moving the needle 12 to the engaged position. Alternatively, the device may output a warning to inform a patient or care-giver that the device is not correctly attached to the skin of a patient. The device 10 can prevent the injection of the needle 12 in an incorrect position which may cause discomfort or pain to a patient.

Figure 4A:
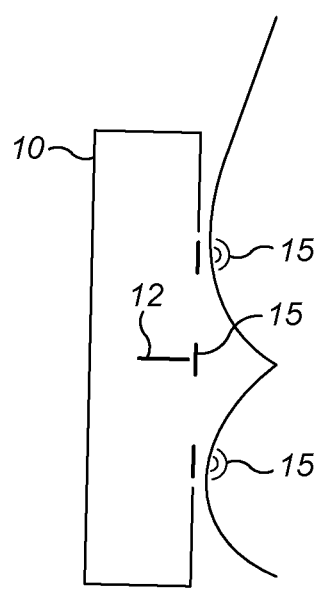
FIG. 4a is a schematic cross-section view of the FIG. 1 device in position on a patient.

FIG. 4A shows the device 10 in an incorrect position on the skin of a patient. The device 10 is shown in an exemplary position on, for example, the abdomen of a patient. The level of the skin is uneven, for instance, the skin may be folded. The lower side 11b of the housing 11 is not flat against the skin. At least one of the sensors 15 is not in contact with the skin. The needle 12 would not pierce the skin in an optimal way if moved into the engaged position.

Figure 4B:
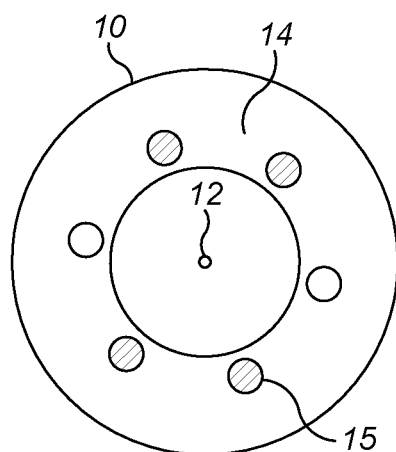
FIG. 4b is a schematic representation of an output of the FIG. 1 device.

As shown in FIG. 4B, two of the six sensors 15 are not activated. The active sensors 15 are in contact with the skin but the inactive sensors 15 are not in contact with the skin. A portion of the sensor array 14 is not activated when the level of the skin is uneven and is not flat against the lower side 11b of the device 10. The needle 12 is not optimally positioned and may cause discomfort if injected in the incorrect position.

The sensor array 14 does not provide a signal which indicates that the device 10 is correctly attached to the skin of a patient. The needle insertion mechanism may be prevented from moving the needle 12 to the engaged position. Alternatively, the device may output a warning to inform a patient or care-giver that the device is not correctly attached to the skin of a patient. The device 10 can prevent the injection of the needle 12 in an incorrect position which may cause discomfort or pain to a patient.

Figure 5:
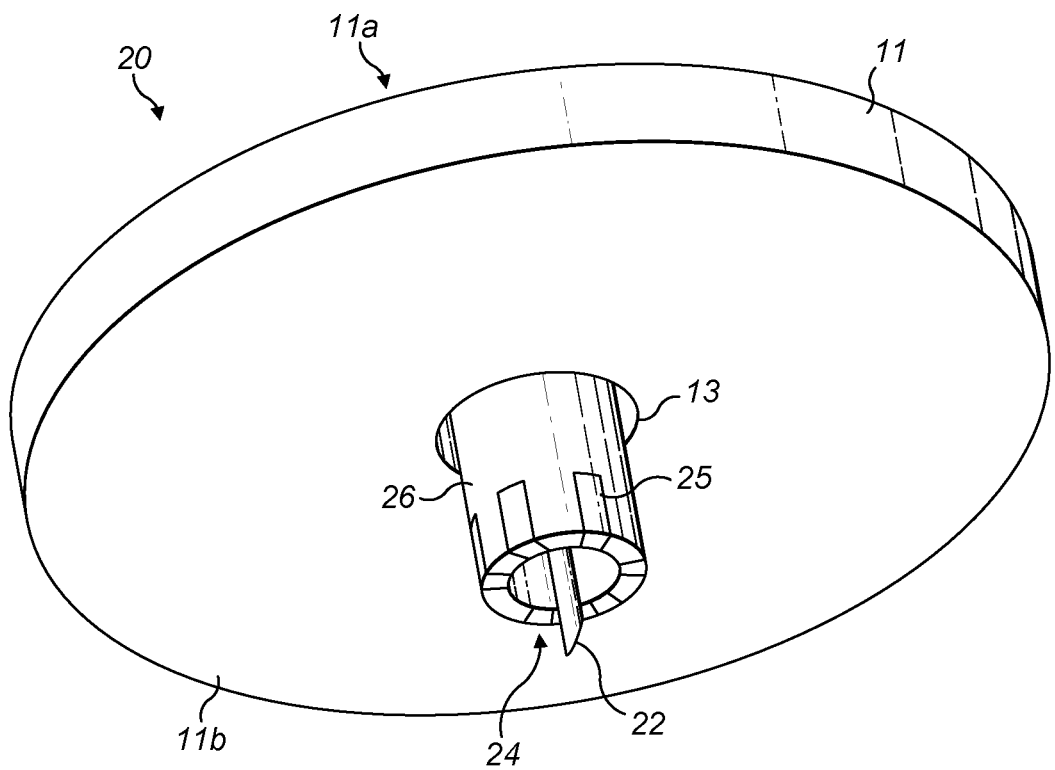
FIG. 5 is an isometric view of a medicament delivery device according to a second embodiment.

With respect to FIG. 5, a medicament delivery device 20 is provided according to a second embodiment. Elements not described below are substantially as described with respect to the first embodiment.

The device 20 comprises a housing 11 an aperture 13, substantially as described above. The device 20 further comprises a needle 22 and a needle shield 26. The needle 22 is substantially as described with respect to the first embodiment. The needle shield 26 is configured to cover the needle 22 when the medicament administration process is complete. The needle shield 26 is an open cylinder arranged to fit around the needle 22 when the needle 22 is in the engaged position.

The needle shield 26 can be retracted through the aperture 13. In a retracted position the needle shield 26 is disposed wholly within the housing 11. In an extended position the needle shield 26 extends from the lower side 11b to surround the needle 22. The needle shield 26 is configured to move from the retracted position to the extended position when the medicament delivery process is complete and the device 20 is detached from the skin of a patient. The needle shield 26 can protect a patient or care-giver from the exposed needle 22 when the device 20 is detached.

The needle shield 26 comprises a sensor array 24. The sensor array 24 is arranged at a lower end of the needle shield 26. The sensor array 24 comprises six sensors 25. The sensor array 24 and the sensors 25 are substantially as described with respect to the first embodiment, and are arranged at the lower end of the needle shield 26. At least a portion of each sensor 25 is disposed on an end face of the needle shield 26. When the needle shield 26 is in the retracted position, the sensors 25 are exposed on the lower side 11b of the housing 11. When the lower side 11b is flat against the skin of a patient, the plurality of sensors 25 make contact with the skin. The sensor array 24 can provide a signal to indicate that the device 10 is placed on the skin of a patient.

Figure 6:
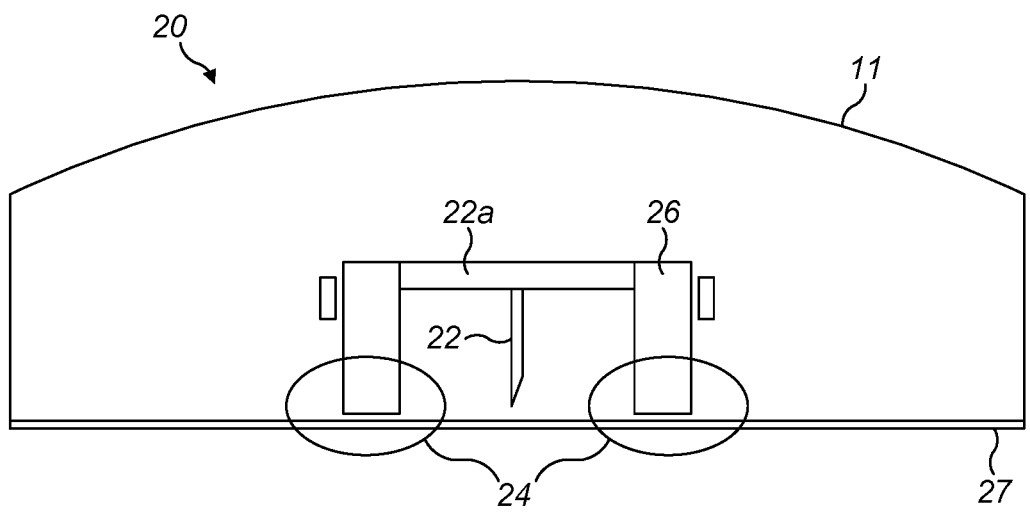
FIG. 6 is a schematic cross-section view of the FIG. 5 device.

FIG. 6 shows the device 20 in an initial state. The needle 22 is in the retracted position. The needle shield 26 is in the retracted position. The device 20 may further comprise a liner 27. The liner 27 is configured to seal the lower side 11b of the device 20 before use. The liner 27 is formed as a thin film layer, for example, a plastic film or a metallic film. The liner 27 is attached to the lower side 11b with an adhesive layer. The liner 27 prevents access to the aperture 13 before the device 20 is used and can prevent interference with the needle 22 through the aperture 13.

The sensor array 24 may be configured to detect the liner 27. The sensor array 24 may provide a signal when the liner 27 is attached to the lower side 11b of the housing 11. The signal provided may be the same as the signal to indicate contact with the skin, or may be a distinct signal. The sensor array 24 may be configured to differentiate between the liner 27 and the skin of a patient.

Figure 7:
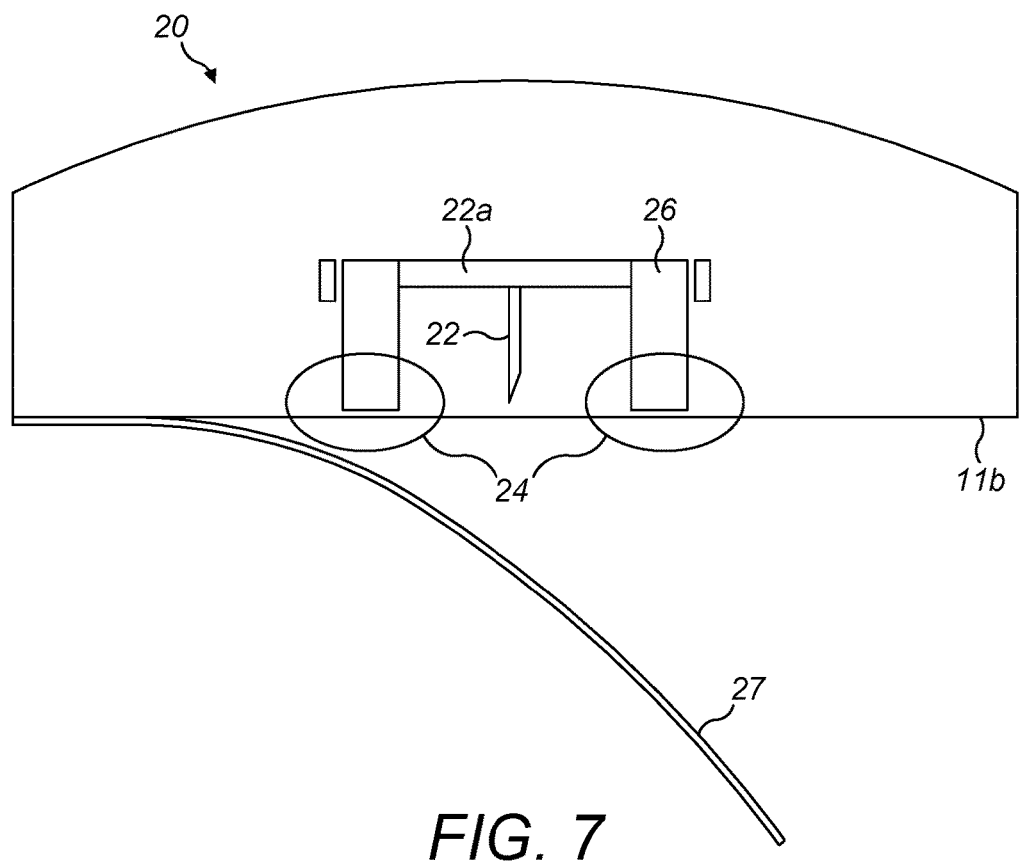
FIG. 7 is a schematic cross-section view of the FIG. 5 device.

FIG. 7 shows the device 20 as the liner 27 is removed. The sensor array 24 is configured to detect that the liner 27 is no longer in contact with the housing 11. The device 10 may be activated conditional on a signal provided by the sensor array 24 which indicates that the liner 27 is removed. For example, a signal provided to a controller may indicate that the liner 27 has been removed and the controller may activate a user interface or a heating mechanism, or may prepare the needle insertion mechanism for activation.

Figure 8:
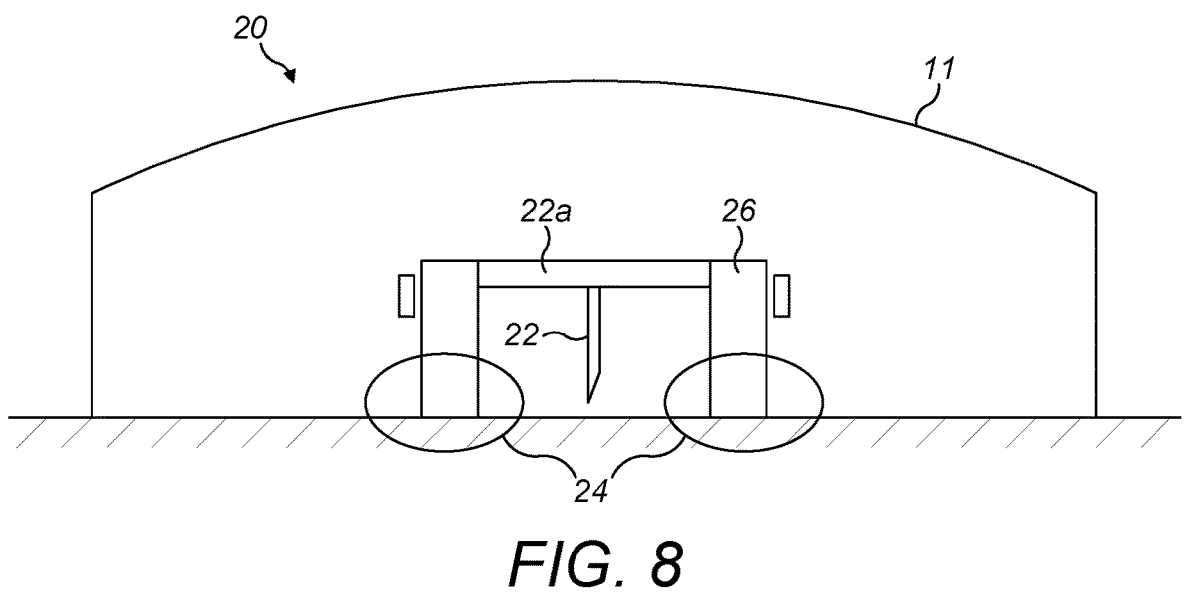
FIG. 8 is a schematic cross-section view of the FIG. 5 device in position on a patient.

FIG. 8 shows the device 20 in position with respect to a patient. The device 20 is shown in a correct position, with the lower side 11b flat against the skin. Each of the sensors 25 is in contact with the skin. The needle 22 is perpendicular to the skin. The needle 22 is shown in the retracted position.

The sensor array 24 can provide a signal which indicates that the device 10 is correctly attached to the skin of a patient. When the sensor array 24 provides a signal indicating that the device 10 is correctly attached, the needle insertion mechanism can be activated to move the needle 22 into the engaged position without causing discomfort. The signal may be provided by the sensor array 24 using an output transducer, to indicate to a patient or care-giver that the needle insertion mechanism can be activated safely. Alternatively, the signal can be provided to a controller, which is configured to activate the needle insertion mechanism automatically in response to the signal. A controller may be configured to activate the needle insertion mechanism when the sensor array 24 detects the liner 27 being removed and the device being attached in succession.

Figure 9:
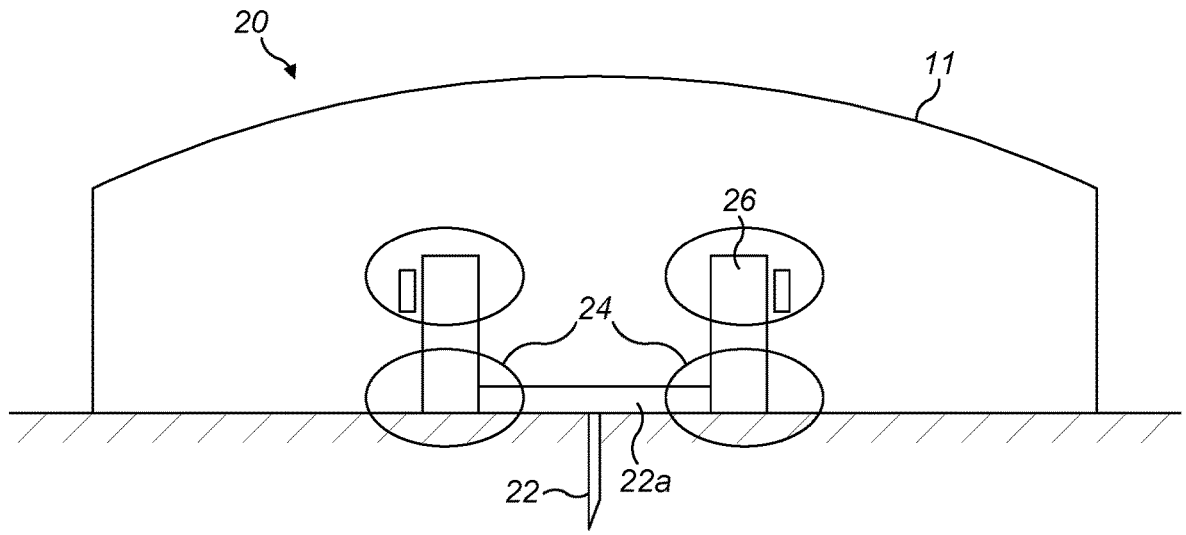
FIG. 9 is a schematic cross-section view of the FIG. 5 device in position on a patient.

FIG. 9 shows the device 20 after activation of the needle insertion mechanism, with the needle 22 in the engaged position. The needle 22 may comprise an engaging portion 22a. The engaging portion 22a is configured to engage with the sensor array 24 when the needle 22 is in the engaged position. The sensor array 24 may be configured to provide a further signal when the needle 22 is moved into the engaged position.

The engaging portion 22a comprises a disc arranged at an upper end of the needle 22. The disc of the engaging portion 22a is formed to fit within the cylinder of the needle shield 26. When the needle shield 26 is in the retracted position and the needle 22 is in the engaged position, the engaging portion 22a is in contact with the plurality of sensors 25. The sensors 25 may be configured to differentiate between contact with the skin and contact with the engaging portion 22a.

The sensor array 24 can provide the signal to indicate that the needle 22 is in the engaged position. The needle 22 may not be in the engaged position if, for example, the needle is obstructed. If the needle 22 is not in the engaged position, the device 10 may not be in the optimal position for delivering the medicament. The sensor array 24 can provide the signal to indicate that the needle 22 is in the engaged position, and the medicament can be safely delivered through the needle. The signal may be provided by the sensor array 24 using an output transducer, to indicate to a patient or care-giver that the medicament delivery mechanism can be activated safely. Alternatively, the signal can be provided to a controller, which is configured to activate the medicament delivery mechanism automatically in response to the signal. A controller may be configured to activate the needle insertion mechanism when the sensor array 24 detects the engaging portion 22a in addition to detecting contact with the skin.

Figure 10:
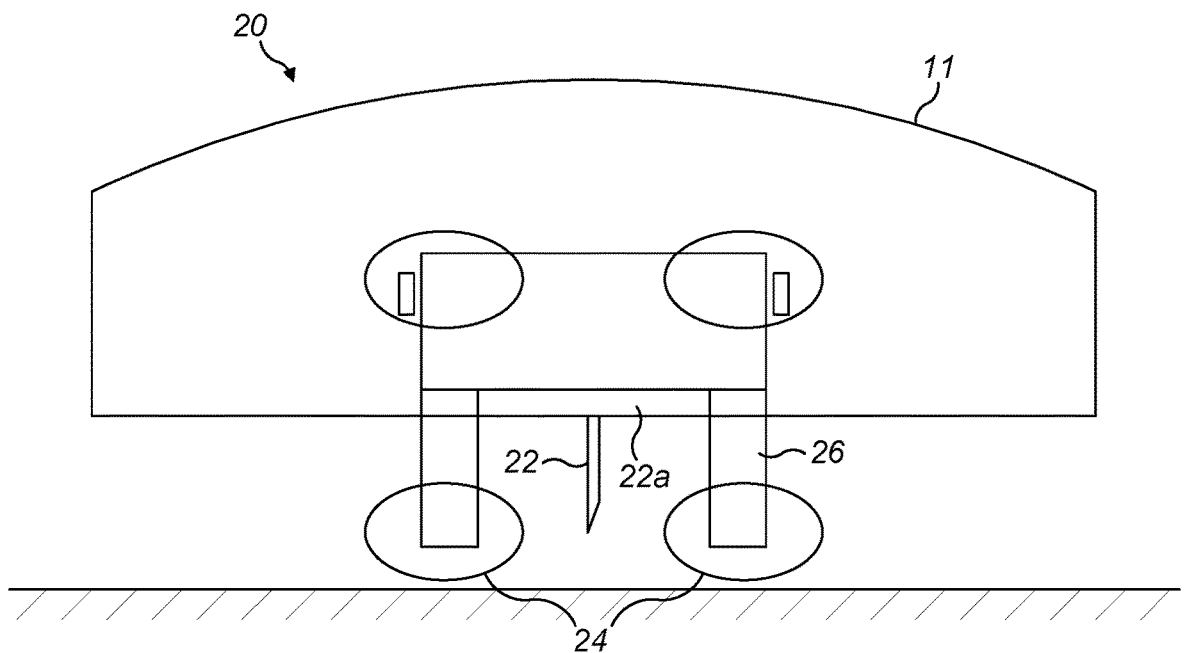
FIG. 10 is a schematic cross-section view of the FIG. 5 device.

FIG. 10 shows the device 20 after the medicament delivery process has been completed. The device 20 is detached from the skin of the patient. The needle 22 remains in the engaged position. The needle shield 26 is moved to the extended position when the device 20 is detached from the skin of the patient. The needle shield 26 may be configured to move to the extended position conditional on the signal provided by the sensor array 24. When the sensor array 24 no longer provides the signal indicating that the device 20 is attached to the skin, the needle shield 26 is moved to the extended position. The needle shield 26 may be operated by a controller or may comprise a logic circuit to monitor the sensor array 24.

Alternatively, the needle shield 26 may be activated mechanically. The needle shield 26 may comprise a spring to urge the needle shield 26 to the extended position. The needle shield 26 may be initially locked in the retracted position and activation of the needle insertion mechanism or medicament delivery mechanism may unlock the needle shield 26. The unlocked needle shield 26 may be retained within the housing 11 by contact with the skin until the device 20 is detached from the skin.

The needle shield 26 can cover the exposed needle 22 when the device 20 has been used. The needle shield 26 can protect a patient or care-giver from the exposed needle 22 when the device 20 is detached.

Although a few embodiments of the present invention have been shown and described, it will be appreciated by those skilled in the art that changes may be made in these embodiments without departing from the invention, the scope of which is defined in the appended claims. Various components of different embodiments may be combined where the principles underlying the embodiments are compatible.

For example, where the sensor array has been described with six sensors, any number of sensors may be used. The sensor array may include one sensor which extends over the entire area of the depicted sensor array. The sensor array may include two sensors situated on opposite sides of the aperture. Where the housing has a clear long axis and a short axis, the device may be stable along the long axis and unstable along the short axis, therefore the two sensors may be aligned with the short axis.

Alternatively, the sensor array may include three or more sensors spaced evenly around the sensor array. The sensor array may have any shape, with the sensors arranged in a circle, a square or any other shape. The sensor may be elongate along one axis or may be irregular in shape.

The device may include a plurality of needles in a needle array. The needle of any embodiment may include the engaging portion for engaging with the sensor array.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The term "drug delivery device" shall encompass any type of device or system configured to dispense a drug or medicament into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, microneedle), inhaler (e.g., nasal or pulmonary), an implantable device (e.g., drug- or API-coated stent, capsule), or a feeding system for the gastro-intestinal tract. The presently described drugs may be particularly useful with injection devices that include a needle, e.g., a hypodermic needle for example having a Gauge number of 24 or higher.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refer to any substance which is sufficiently structurally similar to the original substance so as to have substantially similar functionality or activity (e.g., therapeutic effectiveness). In particular, the term "analogue" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N-(N-lithocholyl-gamma-glutamyl)-des(B30) human insulin; B29-N-(ω-carboxyheptadecanoyl)-des(B30) human insulin and B29-N-(ω-carboxyhepta¬decanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An example of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigens. The antibody can be polyclonal, monoclonal, recombinant, chimeric, de-immunized or humanized, fully human, non-human, (e.g., murine), or single chain antibody. In some embodiments, the antibody has effector function and can fix a complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in certain embodiments include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

The invention claimed is:

1. A method of delivering a medicament from a large volume device, the method comprising:
sensing, using a plurality of sensors of the large volume device, when the large volume device is placed on and attached to skin of a patient, wherein the plurality of sensors is arranged around a needle aperture of the large volume device, and wherein the large volume device is configured to deliver a volume of the medicament of at least two milliliters through a needle of the large volume device during a medicament administration process;
providing a signal when the large volume device is placed on the skin of the patient; and
conditional on the signal, unlocking a retractable needle shield disposed around the needle aperture to move the retractable needle shield from a first position, in which the retractable needle shield is retracted within a housing of the large volume device prior to the housing being placed on the skin of the patient, to a second position, in which the retractable needle shield surrounds the needle of the large volume device.

2. The method of claim 1, further comprising:
activating a plunger driver for the delivering of the medicament through the needle, conditional on the signal.

3. The method of claim 1, further comprising:
moving the needle through the needle aperture, from an initial position where the needle is disposed within the housing, to an engaged position where the needle extends from the housing.

4. The method of claim 3, further comprising:
sensing, using the plurality of sensors, when the needle is in the engaged position; and
providing a further signal when the needle is in the engaged position.

5. The method of claim 3, wherein a portion of the needle is configured to engage with the plurality of sensors when the needle is in the engaged position, and wherein the method further comprises:
sensing that the portion of the needle is engaged with the plurality of sensors using the plurality of sensors when the needle is in the engaged position.

6. The method of claim 5, wherein the plurality of sensors is configured to differentiate between (i) the plurality of sensors being in contact with the skin and (ii) the plurality of sensors being in contact with the portion of the needle.

7. The method of claim 1, further comprising:
delivering the medicament over at least a 10-minute period from the large volume device during the medicament administration process.

8. The method of claim 1, further comprising:
delivering the medicament from the large volume device while the large volume device is attached to the skin of the patient for at least a 5-minute time period.

9. The method of claim 1, wherein the sensing comprises:
sensing when a lower side of the housing of the large volume device is placed against the skin of the patient during the medicament administration process, wherein a width of the lower side of the housing is greater than a height of the large volume device.

10. The method of claim 1, wherein the large volume device is disc-shaped.

11. The method of claim 1, wherein the providing of the signal comprises providing the signal by an output transducer of the large volume device.

12. The method of claim 1, wherein the plurality of sensors is disposed on the retractable needle shield.

13. The method of claim 1, wherein the large volume device comprises a medicament reservoir and the medicament retained in the medicament reservoir.

14. The method of claim 1, further comprising:
responsive to the signal, providing an audio output for indicating that the large volume device is attached to the skin of the patient.

15. The method of claim 1, further comprising:
responsive to the signal, providing a visual output for indicating that the large volume device is attached to the skin of the patient.

16. The method of claim 1, wherein the unlocking of the retractable needle shield is conditional on the signal indicating that at least a threshold number of sensors of the plurality of sensors are in contact with the skin, the threshold number being greater than one.

17. The method of claim 1, further comprising activating the large volume device in response to determining that a liner of the large volume device has been removed.

18. The method of claim 17, wherein the activating of the large volume device comprises activating a user interface of the large volume device.

19. The method of claim 17, wherein the activating of the large volume device comprises activating a heating mechanism of the large volume device.

* * * * *

UNITED STATES PATENT AND TRADEMARK OFFICE
CERTIFICATE OF CORRECTION

| | | |
|---|---|---|
| PATENT NO. | : 12,337,144 B2 | Page 1 of 1 |
| APPLICATION NO. | : 18/638166 | |
| DATED | : June 24, 2025 | |
| INVENTOR(S) | : Michael Schabbach et al. | |

It is certified that error appears in the above-identified patent and that said Letters Patent is hereby corrected as shown below:

On the Title Page

Column 2, Line 1, under "(57) ABSTRACT", after "includes a", delete "device"

Column 2, Line 2, under "(57) ABSTRACT", after "the", delete "device"

Column 2, Line 3, under "(57) ABSTRACT", after "injecting", delete "5"

Column 2, Line 5, under "(57) ABSTRACT", after "the", delete "device"

Signed and Sealed this
Twelfth Day of August, 2025

Coke Morgan Stewart
*Acting Director of the United States Patent and Trademark Office*